United States Patent [19]

Mia

[11] 4,096,037

[45] Jun. 20, 1978

[54] ARGINASE TEST

[75] Inventor: Abdus Salam Mia, Fairless Hills, Pa.

[73] Assignee: Pitman-Moore, Inc., Washington Crossing, N.J.

[21] Appl. No.: 689,237

[22] Filed: May 24, 1976

[51] Int. Cl.$^2$ .............................................. G01N 31/14
[52] U.S. Cl. .............................................. 195/103.5 R
[58] Field of Search ................................ 195/103.5 R

[56] References Cited

PUBLICATIONS

Clinical Enzymology, vol. 2, pp. 121–128, by Romon et al., (1970).

Primary Examiner—Alvin E. Tanenholtz
Attorney, Agent, or Firm—Salvatore R. Conte

[57] ABSTRACT

An improved method for determining the concentration of arginase in serum.

A test sample is treated stepwise with several reagents, including arginine, to produce an ornithine containing solution and the resulting sample is colorimetrically compared against a similar sample absent ornithine. From the resulting measurements an assay for arginase is computed.

The improvement in this method lies principally in the elimination of a centrifugation and precipitation step and, also, in the elimination of a trichloroacetic acid reagent; thus affording an appreciably shorter assay procedure. In addition, this method utilizes less of a serum sample than is required in comparable assay procedures.

19 Claims, No Drawings

ARGINASE TEST

This invention relates to a novel method for assaying the concentration of arginase in serum. There is a correlation between arginase levels in blood serum and liver disease and the instant method provides a reliable and efficient means for measuring those levels and estimating the degree of hepatic necrosis.

BACKGROUND

Arginase is an enzyme which is associated with liver cells and its presence in serum is generally regarded as an indication of liver disease.

Accordingly, various means have been attempted for measuring arginase levels in animals. However, attempts to assay arginase per se have proved unreliable because it is an enzyme which can be inactivated or lost during isolation; therefore, any procedure which relies upon a direct measurement cannot assure that the results accurately reflect the concentration of arginase in the original sample.

Consequently, the search for a reliable test has taken other approaches. One of these consists of measuring the products which arginase is known to produce. It is known, for example, that arginase hydrolyzes serum arginine to urea and ornithine and, as a result, considerable effort has been expended in developing an assay which can reliably measure the ornithine and urea produced from a given amount of L-arginine:

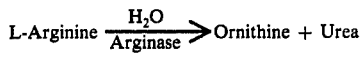

However, efforts at measuring the urea product of this reaction are impractical because of the residual urea normally present in serum.

Therefore, various methods have been attempted at measuring the ornithine product of that reaction. Unfortunately, however, direct spectrophotometric measurements have proved unsuccessful because the spectral curve of ornithine is so similar to that of arginine that it cannot serve as a reliable basis for routine testing.

One method which has proved moderately successful is the procedure of W. Roman and J. Ruys reported in Clinical Enzymology, Vol. 2: pages 121-128 (1970). This procedure consists of treating an arginase-containing serum sample with L-arginine to produce urea and ornithine. The resulting sample is subsequently treated with trichloroacetic acid and a ninhydrin indicator in acidic medium to produce a colored ornithine-ninhydrin complex which can be spectrophotometrically measured.

By measuring the optical density of both the test sample and a blank in which no enzymatic reaction has taken place, the concentration of ornithine in the test material can be determined. From this measurement an assay for arginase can be computed.

Although this method is reliable, it is cumbersome and cannot be used with the efficiency which is generally required in large scale testing and routine clinical studies.

One difficulty lies in the fact that a precipitation and centrifugation step must be conducted in order to obtain a clear supernatant liquid suitable for spectrophotometric comparison.

One other drawback is the need to utilize trichloroacetic acid as one of the reaction ingredients. In addition to its very corrosive and caustic properties, trichloroacetic acid, even of analytical grade, generally contains side products which interfere with the ornithine assay.

THE INVENTION

This invention relates to a new and improved method of quantitatively determining the concentration of arginase in blood serum.

More precisely, this invention covers an improvement in the known methods for determining arginase concentration. By virtue of this improvement, the precipitation and centrifugation or gel filtration steps heretofore required, are now eliminated. As a result, the present method offers the advantages of a shorter test period than was heretofore possible. Whereas, known methods consume from about 68-72 minutes per study, the time required in this procedure is on the order of from about 45-50 minutes. This test is applicable with numerous species of animals and it is specific for determining cell damage in the active stage.

Also, the use of trichloroacetic acid is not required in the present method. Indeed, this method requires only three reagents and a calibration solution.

Another advantage to the present method lies in the relatively minor quantities of serum needed for test purposes. Thus, thoroughly reliable studies can be conducted using approximately one half the amounts required by known methods.

The principle underlying this invention is based on the premise that arginase catalyzes the conversion of L-arginine to urea and ornithine in blood serum. By measuring the amount of ornithine produced from a given amount of serum (test sample) and comparing it against a blank, that is, one in which no enzymatic reaction has occurred (and therefore, no ornithine produced), an estimation can be made of the degree of hepatic damage in the host animal. These measurements are made on a spectrophotometer and, therefore, it is essential that the test and blank samples be treated with identical concentrations of reagents under similar conditions. The volume of the reagents and the concentrations of the ingredients may be varied to a certain extent as, for example, up to 35% but, the methodology, including the calibration procedure which is yet to be discussed, must be performed in the same manner each time.

Essentially, the method of this invention is an improvement over known methods for determining arginase concentration in serum. In general, it consists of measuring, by colorimetric analysis, the ornithine produced from a given amount of serum and comparing it against a similar sample in which no ornithine has been produced. On the basis of this comparison, the concentration of arginase in the serum is estimated.

As a practical matter, the serum which is to be analyzed by this method must be treated with several reagents in order to make it colorimetrically viable; therefore, in practice, the serum is first treated with an activator, then with a buffering agent and, finally, with a coloring additive, whereupon, the resulting mixture is then subjected to colorimetric analysis on a spectrophotometer and the arginase concentration computed.

More specifically, the improvement of this invention consists essentially of:

(1) incubating a sample of blood serum containing magnesium chloride;

(2) adding to said sample an aqueous solution comprising a basic medium, a preservative and L-arginine or a salt of L-arginine, and incubating same;

(3) adding a color developer to said sample and subjecting the mixture to incubation; whereafter, the sample is cooled and colorimetrically compared against a similar sample, absent ornithine, so as to estimate the arginase concentration.

This method has application to mammalian animals in general and studies have been conducted which show its usefulness in determining the hepatic condition in the canine, feline, equine, bovine, porcine and ovine species of animals.

The studies on these species were conducted with mature animals. Acute hepatic damage was established in several animals from each species and the biochemical tests were conducted on a daily basis over a period of several days. The hepatic damage was induced by orally administering a 50% by volume concentration of carbon tetrachloride in mineral oil. Blood samples were collected both before and after the administration of the carbon tetrachloride solution.

Essentially, the test method comprises the following sequence of steps:

(1) placing an aqueous solution of magnesium chloride in both of two tubes, one a Test tube and the other a Blank;

(2) adding a serum sample to both the Test and the Blank tube;

(3) incubating the Blank and Test samples at temperatures approximating body temperature;

(4) adding to the Test sample only an aqueous solution of a buffered substrate comprising a basic medium, L-arginine or a salt thereof and a preservative;

(5) incubating the Test and Blank samples at temperatures approximating body temperature;

(6) adding a color developer to both the Test and Blank tubes;

(7) adding an aqueous solution of a buffered substrate comprising a basic medium, L-arginine and a preservative to the Blank sample only;

(8) incubating the Test and Blank sample at temperatures in the range of 85°–100° C;

(9) cooling the Test and Blank samples;

(10) reading the optical density of the Test sample in a spectrophotometer at a chosen wavelength;

(11) constructing a calibration curve on graph paper or mathematically determining the relationship from the absorbance readings of several calibration samples containing known amounts of ornithine, and their calculated arginase concentration equivalents; and

(12) determining the concentration of the Test sample by locating its absorbance on one axis, determining its intersect on the calibration curve, and then reading the test sample concentration from the axis which recites the arginase concentration equivalents.

The Reagents: The materials needed to conduct this test consist essentially of three Reagents and a calibration solution. The concentrations of these Reagents are expressed on a weight per volume (w/v) basis:

(a) Reagent I is an activator consisting essentially of magnesium chloride dissolved in distilled water. The concentration of this material may vary within a range of from about 0.10–0.40% w/v but a 0.13–0.27% w/v solution is preferred. And in a particularly preferred aspect of this invention, a 0.2% w/v solution of magnesium chloride is considered most suitable for clinical studies.

(b) Reagent II is a buffered substrate which comprises from about 0.25–1.0% w/v of L-arginine or a salt thereof dissolved in an aqueous buffer solution consisting essentially of sodium carbonate and sodium bicarbonate. In a preferred aspect of this invention the L-arginine, or salt of L-arginine, is used at a concentration of from about 0.34–0.72% w/v but, most preferably, at a concentration of about 0.53% w/v. The salts of L-arginine which may be used in this procedure include any suitable acid addition salt which, in solution, will provide the required concentration of L-arginine. Suitable salts include, for example, the hydrohalide salts, such as the hydrochloride or hydrobromide and the like.

The combined concentration of the buffering agents ($Na_2CO_3$ and $NaHCO_3$) is in the range of from about 0.70–1.75% w/v but, preferably, 1.1% w/v. Considered separately, the ratio of the buffers to one another is in the range of from about 15–25 parts by weight of sodium carbonate to about 1 of sodium bicarbonate. By maintaining the buffering agents within those limits the pH of Reagent II can be held within the desired range of 10–11. The preferred pH of 10.5 is achieved by simply maintaining the carbonate/bicarbonate ratio at approximately 20 parts sodium carbonate to one part sodium bicarbonate. Also included in Reagent Ii is a preservative such as sodium azide. This ingredient is most effectively present at a concentration of from about 1/3,500 to about 1/10,000% w/v.

(c) Reagent III is the color developer. It comprises an aqueous solution of from about 0.15–1.0% ninhydrin, from about 50–91% acetic acid and from about 0.75–1.50% phosphoric acid; however, in its preferred concentration, it comprises 0.75% ninhydrin, 91% acetic acid and 1.1% phosphoric acid.

(d) The calibration solution comprises L-ornithine at a concentration of from about 0.009–0.068% w/v (0.5–4.0mMoles) and approximately 0.02% w/v sodium azide as a preservative. In a preferred aspect of this invention the L-ornithine is present at a concentration of about 0.034% w/v (2mMoles).

The activator Reagent I contains magnesium chloride as the principle ingredient. Manganese, cobalt and cadmium also activate arginase in varying degrees; but, for the purpose of this invention, magnesium ions have been found to provide the most desirable activating influence.

The conditions: The time gradients and incubation temperatures used in this method may be varied to a certain extent. However, once the time period has been set it should be followed consistently throughout the study. As a general rule, the incubation time may be varied from 25–50% but, in practice, the incubation periods will depend largely upon the stage of the arginase assay. For example, when activator Reagent I is added to the serum sample the incubation is preferably conducted for about 5 minutes. The second incubation, that is, the one following the addition of the buffered substrate (Reagent II), is also conducted over a fixed period as, for example, over a period of about 20 minutes. Finally, the third and last incubation, which follows the addition of the color developer (Reagent III), is maintained for a period of about 15 minutes.

Also, in general, the incubation temperatures may be varied within a range of from about 3°–12° of the preferred temperature depending upon the stage of the incubation. Thus, for example, the incubation temperatures following the addition of Reagent I and II is most desirably maintained at 37° C, that is, at a level which approximates body temperature, but a few degrees variation above and below that temperature as, for example, within a range of from about 25°–40° C but, preferably, 35°–39° C is acceptable so long as it is followed consistently. The incubation which follows the addition of Reagent III is maintained at 93°–97° C but most preferably at 95° C. However, in practice, a range of from about 85°–100° C is also acceptable.

Procedure: In general, this method consists of several phases in which the serum sample is (1) treated with an activator (Reagent I), then (2) with a buffered substrate (Reagent II) and, lastly, (3) with a color indicator (Reagent III). The product of this method is then measured on a spectrophotometer by reading the optical density of the test sample; and the arginase concentration is determined from that reading by the use of a calibrated curve.

Prior to the actual testing two sample tubes are set up. The first is a "Test" tube to hold the serum sample whose arginase concentration is to be determined; and the second is a "Blank" tube maintained for comparative purposes. The Blank is given all of the Reagents of the Test, at the same concentration levels and under identical conditions, but due to the order in which the Reagents are added, the Blank will not support the production of ornithine. This method will now be described in general terms.

Test Method: In the first or activation phase of this method equal amounts of serum are put into the Test and Blank tubes and both samples are treated with activator Reagent I and then incubated. By including a serum Blank in which no ornithine is produced, it is possible to measure the subsequent increase in optical density due to the formation of ornithine in the Test sample.

The amount of serum employed in this method can be in the range of from about 20–200 microliters, but, preferably, 35–100 microliters. However, in practice, it is most desirable to use a serum sample which measures about 50 microliters.

In the second phase, the Test sample alone is treated with the buffered substrate of Reagent II and then both the Test and Blank samples are incubated at about 37° C. Upon contacting the arginase-containing serum in the Test tube with the L-arginine hydrochloride of Reagent II and enzymatic hydrolysis occurs which results in the formation of ornithine. No ornithine is produced in the Blank. Thereafter, both the Test and Blank samples are subject to a second incubation at about 37° C to assure the completeness of the reaction in the Test sample.

In the third phase, the color developer of Reagent III is added to the Test and Blank samples. Upon the addition of Reagent III the samples in the Test tube and the Blank tube become fixed as the enzymatic reaction is brought to a halt. The acidic ninhydrin Reagent forms a pink colored complex with the ornithine in the Test tube and thus provides a colorimetrically viable sample which is used to assay arginase activity. Absent ornithine production in the Blank, no such ninhydrin complex is formed therein.

To maintain a comparative equivalence between the Test and Blank samples, the buffered substrate (Reagent II) which was omitted from the Blank in the second phase, is added thereto. The Test and Blank samples are then incubated at about 95° C for about 15 minutes and then cooled in running tap water.

After cooling, the optical density of the Test sample is read in a spectrophotometer at a chosen wavelength. (Note: Although maximum optical density occurs at 515 nm, in these studies 530 nm was chosen as a matter of convenience). The concentration of arginase in the serum sample is determined from the optical density readings by constructing a calibration curve from the absorbance readings of several calibration samples and their calculated arginase concentration equivalents. The preparation of the calibration curve is set forth in the following description:

Calibration Curve: The calibration curve referred to in the "Test Method" (supra) is based on the colorimetric calculation of arginase as determined from the absorbance readings of several ornithine-containing samples against a Blank. According to this procedure, activator (Reagent I) and buffered substrate (Reagent II) are added to four tubes labeled Blank, Calibration Solution I, Calibration Solution II, and Calibration Solution III.

Ornithine is then added only to the Calibration Solutions I, II and III. Thereafter, color developer (Reagent III) is added to the Blank and to all three Calibration samples (I, II and III) and the Blank and Calibration samples are incubated to develop the color of the solutions. The Blank and Calibration samples are then cooled in tap water.

The optical densities (i.e., absorbancies) of the three Calibration samples are then read in spectrophotometer at the chosen wavelength (530 nm) against the Blank. The optical density readings thus obtained are plotted as points on a graph paper using the readings and the known arginase concentration values (expressed in IU/L) as fixed parameters. A calibration curve is then plotted by connecting the points on the graph (beginning from zero). From this information the arginase level in the serum samples can be determined.

The preparation of a typical calibration curve is illustrated by the data in Table I below and in Graph 1 which follows. This curve is illustrative only and, in practice, it is necessary to construct a new curve for each new study.

Table I

| Calibration Sample | Absorbance (nm) | Arginase Concentration (IU/L) |
|---|---|---|
| Sample I | 0.140 | 40 |
| Sample II | 0.340 | 100 |
| Sample III | 0.660 | 200 |

GRAPH 1

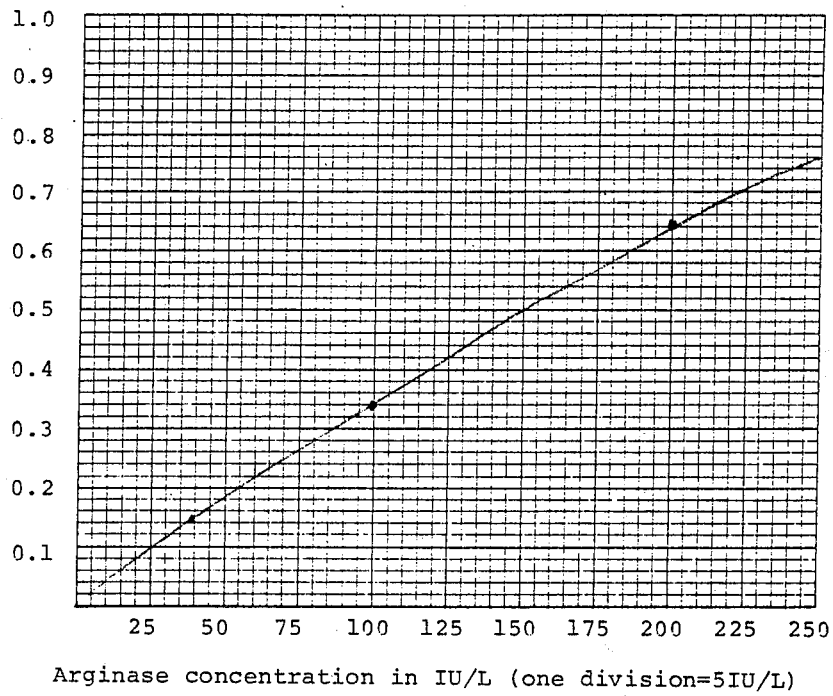

Arginase concentration in IU/L (one division=5IU/L)

Determination of "Test Concentration": The arginase concentration of any "Test" sample can be determined from the calibration curve by simply locating the absorbance of the "Test" sample on the vertical axis. An imaginary horizontal line is then extended from the absorbance reading to the calibration curve. Then one drops vertically from this intersect to the horizontal axis to read the arginase concentration of the "Test".

When used acording to directions, there are no known limitations to this arginase test method. It is applicable in most species of animals for detecting acute liver damage and it has the added advantage of offering an eraly prognostic determination. Coefficients of variation were less than 8% in runs using samples with concentrations between 10–150 IU/L.

The instant method is a distinct improvement over known means for determining arginase levels. It relies upon replicate testing and, as such, it lends itself to being put up in a kit form. The test is compatible with the principal spectrophotometers presently used in laboratory analysis; and the arginase test Reagents I, II and III can be stored over relatively long periods by simply putting them under refrigeration (36°–46° F). Furthermore, arginase-serum samples are stable for seven days at refrigerator temperatures, and only 100 microliters of serum are required per test.

With the exception of a spectrophotometer and test tubes, the principal materials in a typical kit would be the following:
1. Arginase Reagents I, II and III.
2. Droppers (1ml and 3ml).
3. Arginase Calibration Solution.
4. Graph Paper.

This invention will now be described by reference to specific examples. However, it is to be understood that the examples which follow are illustrative only and they are not presented by way of limitation. Any modification of this method which involves simply a variation in the concentration of the reagents or a change in the reaction times or some other such minor adaption, is considered as being within the scope of this invention.

EXAMPLE 1: DETERMINATION OF ARGINASE CONCENTRATION

Step A: Arginase Test Method (1) A 0.2% aqueous solution of magnesium chloride (Regent I) (5 drops; 0.25 ml) is placed in both of two test tubes, one labeled "Blank" and the other labeled "Test". The magnesium chloride serves as an enzyme activator.

(2) Fifty microliters of a serum sample is added to both the Blank and the Test tubes. Both tubes are shaken gently to assure that the magnesium chloride activator and serum samples are thoroughly mixed.

(3) Both the Blank and Test tubes are incubated for five minutes at 37° C to assure the activation of the arginase enzyme.

(4) After the five minute incubation period has expired, 0.5 ml of a buffered substrate is added by means of a graduated dropper to the Test tube only. This buffered substrate has the following composition:

Buffered Substrate (Reagent II)

Buffer:
 1%: Sodium Carbonate
 0.05%: Sodium Bicarbonate
Substrate
 0.53%: L-Arginine Hydrochloride
 0.013%: Sodium Azide (preservative)

(5) After adding the buffered substrate to the Test sample only, both the Test and the Blank are incubated for exactly 20 minutes at 37° C.

(6) After the 20 minute incubation period has passed, 2 ml of a color developer (Reagent III) is added to both the Blank tube and the Test tube via the use of a dropper. This developer has the following composition:

Color Developer (Reagent III)

91%: Acetic Acid
1.1%: Phosphoric Acid
0.75%: Ninhydrin (7) Following the addition of color developer (Reagent III), 0.5 ml of buffered substrate (Reagent II) is added to the Blank only. The composition of this buffered substrate is identical to that described in (4) supra.

(8) The ingredients in the Blank and Test tubes are mixed thoroughly and both are incubated at 95° C for 15 minutes.

(9) Immediately following the 15 minutes incubation period the Blank tube and the Test tube are cooled in cold tap water for five minutes. Thus cooled, the said tubes are ready for colorimetric study.

(10) The optical density of the Test tube is read in a spectrophotometer at a wavelength of 530 nm against the Blank.

(11) The amount of arginase in the Test serum sample is determined by plotting the optical density against the calibration curve obtained by the procedure described in Step B infra.

Step B: Preparation of the Calibration Curve (1) Five drops of Arginase Reagent I and 0.5 ml of Arginase Reagent II are added into each of four clean, dry tubes labeled "Blank", "Calibration Sample I", "Calibration Sample II" and "Calibration Sample III".

(2) Twenty microliters of arginase calibration solution (2mM-ornithine) is added to Calibration Sample I, 50 microliters of calibration solution is added to Calibration Sample II and 70 microliters of calibration solution is added to Calibration Sample III.

(3) Two ml of Arginase Reagent III is added to each of the Blank and the calibration samples and the solutions in each tube are thoroughly mixed.

(4) The Blank and the calibration samples are then incubated for 15 minutes at 95° C for color development.

(5) Immediately after 15 minutes incubation, the tubes are placed in a cold tap water bath for 5 minutes.

(6) The absorbance or optical density of the three calibration samples is then read off a spectrophotometer at a wavelength of 530 nm against the Blank and recorded. On graph paper (Graph 2, infra) the calibration curve is plotted using the absorbance readings of the three Calibration Samples and their arginase concentration equivalents. The calculated arginase concentration equivalent for Calibration Sample I is 40 IU/L; Calibration Sample II is 100 IU/L; and Calibration Sample III is 140 IU/L. The best fitting line is drawn from zero on the graph through the three points. This test measures a range of from 5–50 IU/L. (Note: If this range is exceeded the sample is diluted 1:5 with a 0.9% saline solution, that is, one part sample to four parts saline; and the test is repeated).

The data in Table II below was obtained by following the above procedure.

Table II

| Calibration Sample | Absorbance (nm) | Arginase Concentration (IU/L) |
|---|---|---|
| Sample I | 0.20 | 40 |
| Sample II | 0.40 | 100 |
| Sample III | 0.50 | 140 |

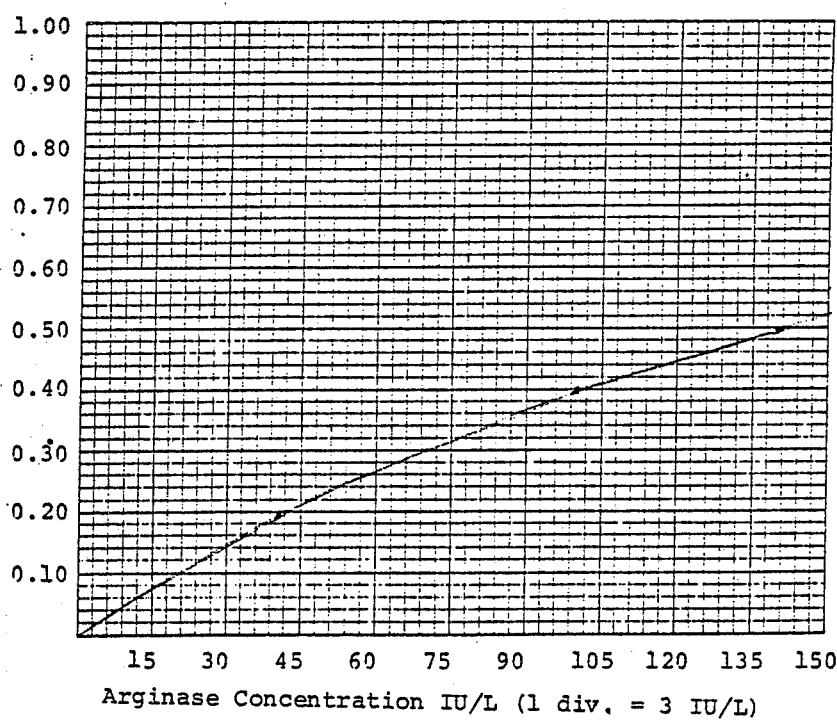

GRAPH 2

Arginase Concentration IU/L (1 div. = 3 IU/L)

Step C: Determination of "Test" Concentration

Naturally Occurring Arginase

The graph of Step B makes it possible to determine the arginase concentration for any "Test" sample prepared according to the procedure of Step A. To determine the arginase concentration the absorbance reading from the Test sample is simply located on the vertical axis and an imaginary line is extended from the said reading to the calibration curve (intersect). To read the arginase concentration it is only necessary to drop vertically from the intersect to the horizontal axis.

Using the method described in Steps A-C the serum arginase concentrations in six species of domestic animals were determined. The results of this study are shown in Table III. In this study the animals were not subjected to experimental liver damage.

In the above Table a high arginase level is indicative of active necrosis. In animals recovering from experimental (induced) liver damage, serum levels of arginase were found to normalize relatively soon indicating that the present test may have an early prognostic value.

What is claimed is:

1. A method for determining the concentration of arginase in blood serum which consists essentially of the steps of:
    (1) incubating a sample of arginase-containing blood serum with an arginase-activating source of magnesium, manganese, cobalt or cadmium ions at 25°-40° C for about five minutes;
    (2) adding to said incubated sample an aqueous buffered solution of L-arginine or an acid addition salt thereof and incubating the mixture at 25°-40° C for a time sufficient for the arginase to catalyze the hydrolysis of said L-arginine to urea and ornithine;
    (3) adding a color developer comprising an acidic aqueous solution of ninhydrin to the thus-obtained ornithine-containing mixture without prior centrifugation and removal of precipitate to form a colored ornithine-ninhydrin complex and incubating the resultant mixture at 85°-100° C for about 15 minutes; and
    (4) after cooling, colorimetrically measuring the amount of said colored complex and calculating the concentration of arginase in the given blood serum sample from said measure.

2. The method of claim 1 wherein the source of magnesium ions in step (1) is magnesium chloride.

3. A method for determining the concentration of

TABLE III

Serum Arginase Concentration in Six Species of Domestic Animals

| Canine | Conc. IU/L | Feline | Conc. IU/L | Bovine | Conc. IU/L | Equine | Conc. IU/L | Ovine | Conc. IU/L | Porcine | Conc. IU/L |
|---|---|---|---|---|---|---|---|---|---|---|---|
| 1 | 0 | 1 | 8 | 1 | 0 | 1 | 3 | 1 | 0 | 1 | 0 |
| 2 | 0 | 2 | 4 | 2 | 0 | 2 | 5 | 2 | 3 | 2 | 0 |
| 3 | 0 | 3 | 0 | 3 | 0 | 3 | 2 | 3 | 0 | 3 | 0 |
| 4 | 5 | 4 | 0 | 4 | 4 | 4 | 2 | 4 | 0 | 4 | 0 |
| 5 | 0 | 5 | 5 | 5 | 0 | 5 | 9 | 5 | 0 | 5 | 0 |
| 6 | 0 | 6 | 0 | 6 | 0 | 6 | 0 | 6 | 0 | 6 | 0 |
| 7 | 4 | 7 | 0 | 7 | 5 | 7 | 6 | 7 | 0 | 7 | 0 |
| 8 | 4 | 8 | 4 | 8 | 0 | 8 | 5 | 8 | 0 | 8 | 3 |
| 9 | 14 | 9 | 0 | 9 | 0 | 9 | 3 | 9 | 0 | 9 | 0 |
| 10 | 6 | 10 | 0 | 10 | 2 | 10 | 4 | 10 | 0 | 10 | 0 |
| 11 | 0 | 11 | 9 | 11 | 0 | 11 | 5 | 11 | 3 | 11 | 0 |
| 12 | 3 | 12 | 0 | 12 | 10 | 12 | 1 | 12 | 0 | 12 | 0 |
| 13 | 3 | 13 | 4 | 13 | 5 | 13 | 1 | 13 | 0 | 13 | 0 |
| 14 | 5 | 14 | 8 | 14 | 5 | 14 | 3 | 14 | 0 | 14 | 0 |
| 15 | 0 | 15 | 7 | 15 | 0 | 15 | 4 | 15 | 0 | 15 | 0 |
| 16 | 0 | 16 | 2 | 16 | 0 | 16 | 7 | 16 | 0 | 16 | 10 |
| 17 | 0 | 17 | 4 | 17 | 5 | 17 | 1 | 17 | 0 | 17 | 0 |
| 18 | 8 | 18 | 4 | 18 | 3 | 18 | 1 | 18 | 9 | | |
| 19 | 6 | 19 | 5 | 19 | 4 | 19 | 3 | 19 | 0 | | |
| 20 | 4 | 20 | 12 | 20 | 0 | 20 | 0 | 20 | 0 | | |
| 21 | 4 | 21 | 5 | | | | | | | | |
| 22 | 5 | 22 | 5 | | | | | | | | |
| | | 23 | 10 | | | | | | | | |
| | | 24 | 5 | | | | | | | | |
| | | 25 | 0 | | | | | | | | |
| Range 0-14 | | Range 0-12 | | Range 0-10 | | Range 0-9 | | Range 0-9 | | Range 0-10 | |

EXAMPLE 2: DETERMINATION OF INDUCED ARGINASE CONCENTRATION

Induced Arginase

In another study, again using the method described in Steps A-C, the serum arginase levels in six species of animals were determined. In this study liver damage was induced by orally administering to the test animals a 50% carbon tetrachloride ($CCl_4$) in mineral oil solution. The $CCl_4$ dosage (ml) was based on the body weight in pounds (lbs.) of the test animal. Table IV summarizes the results of this study. In this instance, the serum arginase levels were determined both before and after the induction of experimental liver damage.

TABLE IV

Serum Arginase Concentration Before and After Experimental Liver Damage

| Species | Dose of $CCL_4$ Ml/Lb. | BEFORE | Serum Arginase Concentration : IU/L AFTER | | | | | | | | | |
|---|---|---|---|---|---|---|---|---|---|---|---|---|
| | | | 18 Hrs. | 24 Hrs. | 36 Hrs. | 48 Hrs. | 60 Hrs. | 72 Hrs. | 96 Hrs. | 5 Days | 6 Days | 7 Days |
| Canine | 0.75 | 7 | 110 | 200 | 680 | 17 | 10 | 0 | 0 | 0 | 0 | 0 |
| Equine | 0.25 | 4 | 24 | 338 | 1700 | 1980 | 3080 | 1440 | 520 | 170 | 0 | 5 |
| Ovine | 0.13 | 0 | — | 140 | — | 25 | — | 0 | 0 | 7 | 0 | |
| Feline | 1.5 | 0 | | | | 43 | | 815 | 15 | 5 | 0 | |
| Bovine | 0.5 | 0 | | 16 | | 178 | | 5 | 0 | 0 | 0 | |
| Porcine | 0.5 | 0 | — | 275 | — | 226 | — | 5 | 0 | 0 | | | arginase in blood serum which consists essentially of the steps of:

(1) incubating a sample of arginase-containing blood serum with an arginase-activating source of magnesium ions at 35°–39° C for about 5 minutes;

(2) adding to said incubated sample an aqueous carbonate buffer solution at pH 10–11 of L-arginine or an acid addition salt thereof and incubating the mixture at 35°–39° C for about 20 minutes in order for the arginase to catalyze the hydrolysis of said L-arginine to urea and ornithine;

(3) adding an acidic aqueous solution of ninhydrin consisting essentially of acetic acid, phosphoric acid and ninhydrin to the thus-obtained ornithine-containing mixture without prior centrifugation and removal of precipitate to form a colored ornithine-ninhydrin complex and incubating the resultant mixture at 93°–97° C for about 15 minutes; and (4) after cooling, colorimetrically measuring the amount of said colored complex and calculating the concentration of arginase in the given blood serum sample from said measure.

4. The method of claim 3 wherein the source of magnesium ions in step (1) is magnesium chloride.

5. The method of claim 3 wherein the source of magnesium ions in step (1) is magnesium chloride; the incubation temperature in both steps (1) and (2) is about 37° C; and the incubation temperature is step (3) is about 95° C.

6. The method of claim 3 wherein the solution of ninhydrin in step (3) consists essentially of 50–90% acetic acid, 0.75–1.50% phosphoric acid and 0.15–1.0% ninhydrin in water.

7. A method for determining the concentration of arginase in blood serum which consists essentially of (1) placing an aqueous solution of magnesium chloride in both of two tubes, one a test tube and the other a blank;

(2) adding a serum sample to both the test and the blank tube;

(3) incubating the blank and test samples at temperatures approximating body temperature for about 5 minutes;

(4) adding to the test sample only an aqueous solution of a buffered substrate comprising a carbonate buffer solution at pH 10–11 of L-arginine or an acid addition salt thereof and a preservative;

(5) incubating the test and blank samples at temperatures approximating body temperature for about 20 minutes;

(6) adding, without prior centrifugation and removal of precipitate, a color developer comprising an acidic aqueous solution of ninhydrin to both the test and blank tubes;

(7) adding an aqueous solution of a buffered substrate comprising a carbonate buffer solution at pH 10–11 of L-arginine or an acid addition salt thereof and a preservative to the blank sample only;

(8) incubating the test and blank samples at a temperature in the range of from about 85°–100° C for about 15 minutes;

(9) cooling the test and blank samples;

(10) reading the optical density of the test sample in a spectrophotometer at a chosen wavelength;

(11) constructing a calibration curve from the absorbance readings of several calibration samples and their calculated arginase concentration equivalents; and

(12) determining the concentration of the test sample by locating its absorbance on one axis, determining its intersect on the calibration curve, and then reading the test sample concentration from the axis which recites the arginase concentration equivalents.

8. A method for determining the concentration of arginase in blood serum which consists essentially of:

(1) placing a 0.10–0.40% w/v aqueous solution of magnesium chloride in both a test tube and a blank tube;

(2) adding a serum sample of from about 20–200 microliters to both the test and the blank tubes;

(3) incubating the blank and test samples for about 5 minutes at a temperature in the range of from about 25°–40° C.

(4) adding to the test sample only an aqueous solution of a buffered substrate comprising a sodium carbonate/sodium bicarbonate buffer at pH 10–11 with L-arginine hydrohalide and a preservative;

(5) incubating the test and blank samples for about 20 minutes at a temperature in the range of from about 25°–40° C.

(6) adding, without prior centrifugation and removal of precipitate, to both the test and blank tubes a color developer consisting essentially of acetic acid, phosphoric acid and ninhydrin in water;

(7) adding an aqueous solution of a buffered substrate comprising a sodium carbonate/sodium bicarbonate buffer at pH 10–11 with L-arginine and a preservative to the blank tube only;

(8) incubating the test and blank samples for about 15 minutes at a temperature in the range of from about 85°–100° C;

(9) cooling the test and blank samples;

(10) reading the optical density of the test sample in a spectrophotometer at a given wavelength;

(11) constructing a calibration curve from the absorbance readings of several calibration samples and their calculated arginase concentration equivalents; and

(12) determining the concentration of the test sample by locating its optical density value on the vertical axis, extending a horizontal line to the calibration curve and from that intersect dropping to the horizontal axis to read the arginase concentration.

9. The method of claim 8 in which the preservative comprising the buffered substrate of steps (4) and (7) is sodium azide.

10. The method of claim 8 in which the serum sample is added to both the test and the blank tube in an amount of from 35–100 microliters.

11. The method of claim 8 in which the buffered substrate of steps (4) and (7) is a composition comprising from about 15–25 parts by weight of sodium carbonate to about one part sodium bicarbonate, from about 0.25–1.0% w/v of L-arginine hydrochloride and from about 1/3,500–1/10,000% w/v of sodium azide as the preservative.

12. The method of claim 11 in which the combined concentration of the sodium carbonate and sodium bicarbonate buffering agents is in the range of from about 0.70–1.75% w/v.

13. The method of claim 8 in which the buffered substrate of steps (4) and (7) is a composition comprising 1% w/v sodium carbonate, 0.05% w/v sodium bicarbonate, 0.53% w/v L-arginine hydrochloride and 1/3,500–1/10,000% w/v sodium azide as the preservative.

14. The method of claim 8 in which the incubation temperature in steps (3) and (5) is from about 35°–39° C.

15. The method of claim 8 in which the incubation temperature in step (8) is from about 93°–97° C.

16. The method of claim 8 in which the color developer of step (6) has the following concentrations of ingredients: 91% acetic acid, 1.1% phosphoric acid and 0.75% ninhydrin in water.

17. The method of claim 8 in which the wavelength for reading the optical density of the Test sample is 530 nm.

18. A method for determining the concentration of arginase in blood serum which consists essentially of:
    (1) placing a 0.2% w/v aqueous solution of magnesium chloride in both a test tube and a blank tube;
    (2) adding a 50 microliter serum sample to both the test and the blank tubes;
    (3) incubating the blank and test samples for about 5 minutes at about 37° C;
    (4) adding to the test sample only an aqueous solution of a buffered substrate comprising 1% sodium carbonate, 0.05% sodium bicarbonate, 0.53% L-arginine hydrochloride and 1/3,500–1/10,000% w/v of sodium azide;
    (5) incubating the test and blank samples for about 20 minutes at about 37° C;
    (6) adding, without prior centrifugation and removal of precipitate, to both the test and blank tubes a color developer consisting essentially of 91% acetic acid; 1.1% phosphoric acid and 0.75% ninhydrin in water;
    (7) adding an aqueous solution of a buffered substrate comprising 1% sodium carbonate, 0.05% sodium bicarbonate, 0.53% L-arginine hydrochloride and 0.013% of sodium azide to the blank tube only;
    (8) incubating the test and blank samples for about 15 minutes at a temperature of about 95° C;
    (9) cooling the test and blank samples;
    (10) reading the optical density of the test sample in a spectrophotometer at a given wavelength;
    (11) constructing a calibration curve from the absorbance readings of several calibration samples and their calculated arginase concentration equivalents; and
    (12) determining the concentration of the test sample by locating its optical density value on the vertical axis, extending a horizontal line to the calibration curve and from that intersect dropping to the horizontal axis to read the arginase concentration.

19. The method of claim 7 in which the materials used for determining the concentration of arginase are assembled in a kit form.

* * * * *

UNITED STATES PATENT AND TRADEMARK OFFICE
CERTIFICATE OF CORRECTION

PATENT NO. : 4,096,037
DATED : June 20, 1978
INVENTOR(S) : Abdus Salam Mia

It is certified that error appears in the above-identified patent and that said Letters Patent are hereby corrected as shown below:

At Column 4, Line 26, "Reagent Ii" should be -- Reagent II --.
At Column 7, Line 45, "eraly" should be -- early --.
At Column 13, Line 32, "50-90%" should be -- 50-91% --.

Signed and Sealed this

Fifteenth Day of May 1979

[SEAL]

Attest:

RUTH C. MASON
Attesting Officer

DONALD W. BANNER
Commissioner of Patents and Trademarks